(12) United States Patent
Ayyat et al.

(10) Patent No.: US 10,970,840 B2
(45) Date of Patent: Apr. 6, 2021

(54) EVALUATION OF LUNGS VIA ULTRASOUND

(71) Applicant: THE CLEVELAND CLINIC FOUNDATION, Cleveland, OH (US)

(72) Inventors: Kamal S. Ayyat, Lakewood, OH (US); Kenneth R. McCurry, Cleveland, OH (US); Toshihiro Okamoto, Beachwood, OH (US); Ajit Moghekar, Chagrin Falls, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 59 days.

(21) Appl. No.: 16/269,389

(22) Filed: Feb. 6, 2019

(65) Prior Publication Data

US 2019/0244356 A1 Aug. 8, 2019

Related U.S. Application Data

(60) Provisional application No. 62/626,975, filed on Feb. 6, 2018.

(51) Int. Cl.
| | |
|---|---|
| *G06T 7/00* | (2017.01) |
| *G06K 9/62* | (2006.01) |
| *G01N 29/44* | (2006.01) |
| *G16H 30/40* | (2018.01) |
| *G16H 50/20* | (2018.01) |

(52) U.S. Cl.
CPC ......... *G06T 7/0016* (2013.01); *G01N 29/449* (2013.01); *G06K 9/628* (2013.01); *G06K 9/6217* (2013.01); *G06K 9/6253* (2013.01); *G16H 30/40* (2018.01); *G16H 50/20* (2018.01); *G01N 2291/02475* (2013.01); *G06T 2200/24* (2013.01); *G06T 2207/10132* (2013.01); *G06T 2207/30061* (2013.01)

(58) Field of Classification Search
CPC ...... G06T 7/0016; G16H 50/20; G16H 30/40; G01N 29/449; G06K 9/6217; G06K 9/6253; G06K 9/628
See application file for complete search history.

(56) References Cited

U.S. PATENT DOCUMENTS

| | | | |
|---|---|---|---|
| 2017/0086794 A1* | 3/2017 | Halmann | G16H 50/30 |
| 2018/0110491 A1* | 4/2018 | Ishida | A61B 6/5264 |

OTHER PUBLICATIONS

Baldi et al, "Lung water assessment by lung ultrasonography in intensive care: a pilot study," 2013, Intensive Care Med (2013) 39: 74-84 (11 pages) (Year: 2013).*

(Continued)

*Primary Examiner* — David F Dunphy
(74) *Attorney, Agent, or Firm* — Tarolli, Sundheim, Covell & Tummino LLP

(57) ABSTRACT

Systems and methods are provided for evaluating a lung via ultrasound. A plurality of ultrasound images are generated at each of a plurality of locations on a lung using an ultrasound imager to provide a plurality of images. Respective grades are assigned to each of the plurality of images according to an amount of B-line artifact in the image to generate a plurality of grades for the lung. A composite score for the lung is calculated from the plurality of grades. The composite score represents a general assessment of the lung. The composite score is provided to a user at an associated output device.

20 Claims, 3 Drawing Sheets

(56) References Cited

OTHER PUBLICATIONS

Bataille, Benoît, et al. "Accuracy of ultrasound B-lines score and E/Ea ratio to estimate extravascular lung water and its variations in patients with acute respiratory distress syndrome." Journal of clinical monitoring and computing 29.1 (2015): 169-176.

Blanco, Pablo A., and Tomas F. Cianciulli. "Pulmonary edema assessed by ultrasound: impact in cardiology and intensive care practice." Echocardiography 33.5 (2016): 778-787.

Bouhemad, Belaïd, et al. "Bedside ultrasound assessment of positive end-expiratory pressure-induced lung recruitment." American journal of respiratory and critical care medicine 183.3 (2011): 341-347.

Daddi, Niccolò, et al. "Ex vivo pulmonary nodule detection with miniaturized ultrasound convex probes." journal of surgical research 202.1 (2016): 49-57.

Duenwald-Kuehl, Sarah, et al. "Ultrasound Assessment of Ex Vivo Lung Tissue Properties Using a Fluid-Filled Negative Pressure Bath." Journal of biomechanical engineering 136.7 (2014): 074504.

Hew, Mark, and Tunn Ren Tay. "The efficacy of bedside chest ultrasound: from accuracy to outcomes." European Respiratory Review 25.141 (2016): 230-246.

Jambrik, Zoltan, et al. "Usefulness of ultrasound lung comets as a nonradiologic sign of extravascular lung water." The American journal of cardiology 93.10 (2004): 1265-1270.

Jambrik, Zoltán, et al. "B-lines quantify the lung water content: a lung ultrasound versus lung gravimetry study in acute lung injury." Ultrasound in medicine & biology 36.12 (2010): 2004-2010.

Koenig, Seth J., Mangala Narasimhan, and Paul H. Mayo. "Thoracic ultrasonography for the pulmonary specialist." Chest 140.5 (2011): 1332-1341.

Lichtenstein, D., and Gilbert Mezière. "A lung ultrasound sign allowing bedside distinction between pulmonary edema and COPD: the comet-tail artifact." Intensive care medicine 24.12 (1998): 1331-1334.

Lopes-Ramos, Camila, et al. "Comprehensive evaluation of the effectiveness of gene expression signatures to predict complete response to neoadjuvant chemoradiotherapy and guide surgical intervention in rectal cancer." Cancer genetics 208.6 (2015): 319-326.

Martindale, Jennifer L., Vicki E. Noble, and Andrew Liteplo. "Diagnosing pulmonary edema: lung ultrasound versus chest radiography." European Journal of Emergency Medicine 20.5 (2013): 356-360.

Moghekar, Ajit, and Atul Mehta. "Thoracic ultrasound: Picture worth a thousand sounds." Annals of thoracic medicine 9.4 (2014): 185.

Picano, Eugenio, and Patricia A. Pellikka. "Ultrasound of extravascular lung water: a new standard for pulmonary congestion." European heart journal 37.27 (2016): 2097-2104.

Reeb, Jeremie, and Marcelo Cypel. "Ex vivo lung perfusion." Clinical transplantation 30.3 (2016): 183-194.

Van Raemdonck, Dirk, et al. "Ex-vivo lung perfusion." Transplant International 28.6 (2015): 643-656.

Volpicelli, Giovanni, et al. "International evidence-based recommendations for point-of-care lung ultrasound." Intensive care medicine 38.4 (2012): 577-591.

Wimalasena, Yashvi, Jeremy Windsor, and Mark Edsell. "Using ultrasound lung comets in the diagnosis of high altitude pulmonary edema: fact or fiction?." Wilderness & Environmental Medicine 24.2 (2013): 159-164.

\* cited by examiner

EVALUATION OF LUNGS VIA ULTRASOUND

RELATED APPLICATIONS

This application claims priority to U.S. Provisional Patent Application Ser. No. 62/626,975 ("the '975 application"), filed Feb. 6, 2018 and entitled DIRECT LUNG ULTRASOUND EVALUATION OF DONOR LUNGS. The entirety of the '975 application is hereby incorporated by reference.

TECHNICAL FIELD

This disclosure relates to medical imaging and, more particularly, to evaluation of lungs via ultrasound.

BACKGROUND

Lung content of extravascular lung water (EVLW) can significantly affect pulmonary functions. Multiple factors can play a role in changing the amount of EVLW like lung injury and hemodynamic status. Additionally, a marked heterogeneity is observed in the distribution of EVLW. It may vary across different areas in the same lung and being more susceptible to collapse and injury, lower lobes might have a higher content of EVLW. Quantification of EVLW in each part of the lungs is crucial for patient management.

The amount of EVLW can change in donor lungs in a time-dependent fashion during the procurement process. For brain dead donors, the EVLW amount can be affected by the proinflammatory response, cardiac dysfunction, ventilator management, or fluid replacement during the donor management period. In the circumstance of donation after circulatory death, hypoxic pulmonary vasoconstriction and profound catecholamine surge occurring after withdrawal of life-sustaining therapy could dramatically change the EVLW content in donor lungs. Importantly, this type of change cannot be assessed accurately in vivo, however, it can adversely affect recipient outcome.

Ex-vivo lung perfusion (EVLP) has emerged as a reliable technology for better assessment of questionable lungs, with therapeutic potentials of the injured lung as well. However, pulmonary edema formation represented by an increase of EVLW is one of the findings of the current EVLP protocols, with reduction of this edema as a targeted therapeutic potential of EVLP.

SUMMARY

In one example, a system includes an ultrasound imager manipulable to image a lung at a plurality of locations to produce a plurality of images, a processor, and a non-transitory computer readable medium storing executable instructions. The executable instructions include a grader interface configured to receive, for each of the plurality of locations, data representing the image or images taken at that location and provide a plurality of grades. Each of the plurality of grades represents the amount of B-line artifact in a corresponding image. A score calculator is configured to determine a composite score representing a general assessment of the lung from the plurality of grades. A user interface is configured to provide the composite score to a user at an associated output device.

In another example, a method is provided. A plurality of ultrasound images are generated at each of a plurality of locations on a lung using an ultrasound imager to provide a plurality of images. Respective grades are assigned to each of the plurality of images according to an amount of B-line artifact in the image to generate a plurality of grades for the lung. A composite score for the lung is calculated from the plurality of grades. The composite score represents a general assessment of the lung. The composite score is provided to a user at an associated output device.

In yet another example, a computer program product stores instructions executable by an associated processor to evaluate a plurality of ultrasound images of a donor lung. The executable instructions include a grader interface configured to receive, for each of the ultrasound images, data representing the image, and provide a grade representing the amount of B-line artifact in the image. A score calculator is configured to determine a composite score representing a general assessment of the lung for transplant from the plurality of grades. A user interface is configured to provide the composite score to a user at an associated output device.

DETAILED DESCRIPTION

Trans-thoracic ultrasonography has been proven to be an accurate adjunct in the diagnosis of a variety of lung pathologies, including pulmonary edema. The air-fluid interface, in the presence of extra-alveolar fluid, caused a degree of artifact within the image referred to, alternatively as an ultrasound lung comet, B-line, or "comet tail" artifact. Current techniques for EVLW evaluation in lungs after procurement and in EVLP settings are either subjective (e.g., intra-operative palpation), a general estimation (e.g., lung weight), or not feasible in the clinical setting (e.g., wet/dry ratio (W/D) measurement). The inventors propose exploiting the B-line artifact produced in B-line measurement to provide an accurate and non-invasive diagnostic tool for monitoring EVLW for lung assessment and management.

Figure 1:
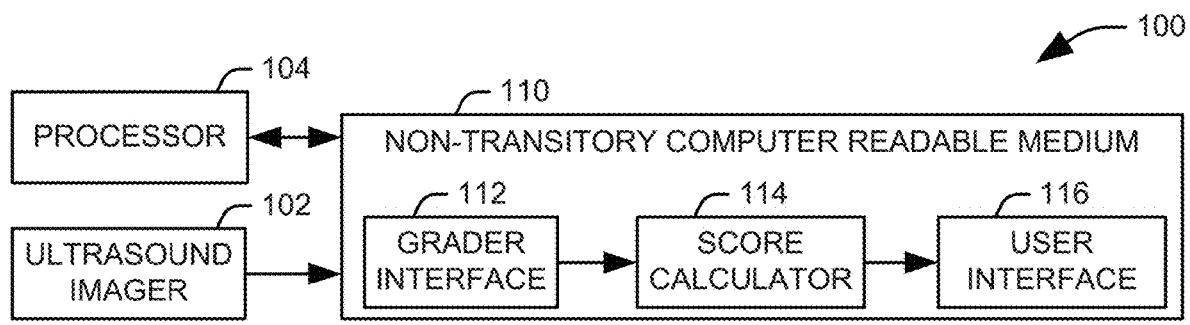
FIG. 1 illustrates a system for evaluating a lung via ultrasound.
Figure 2:
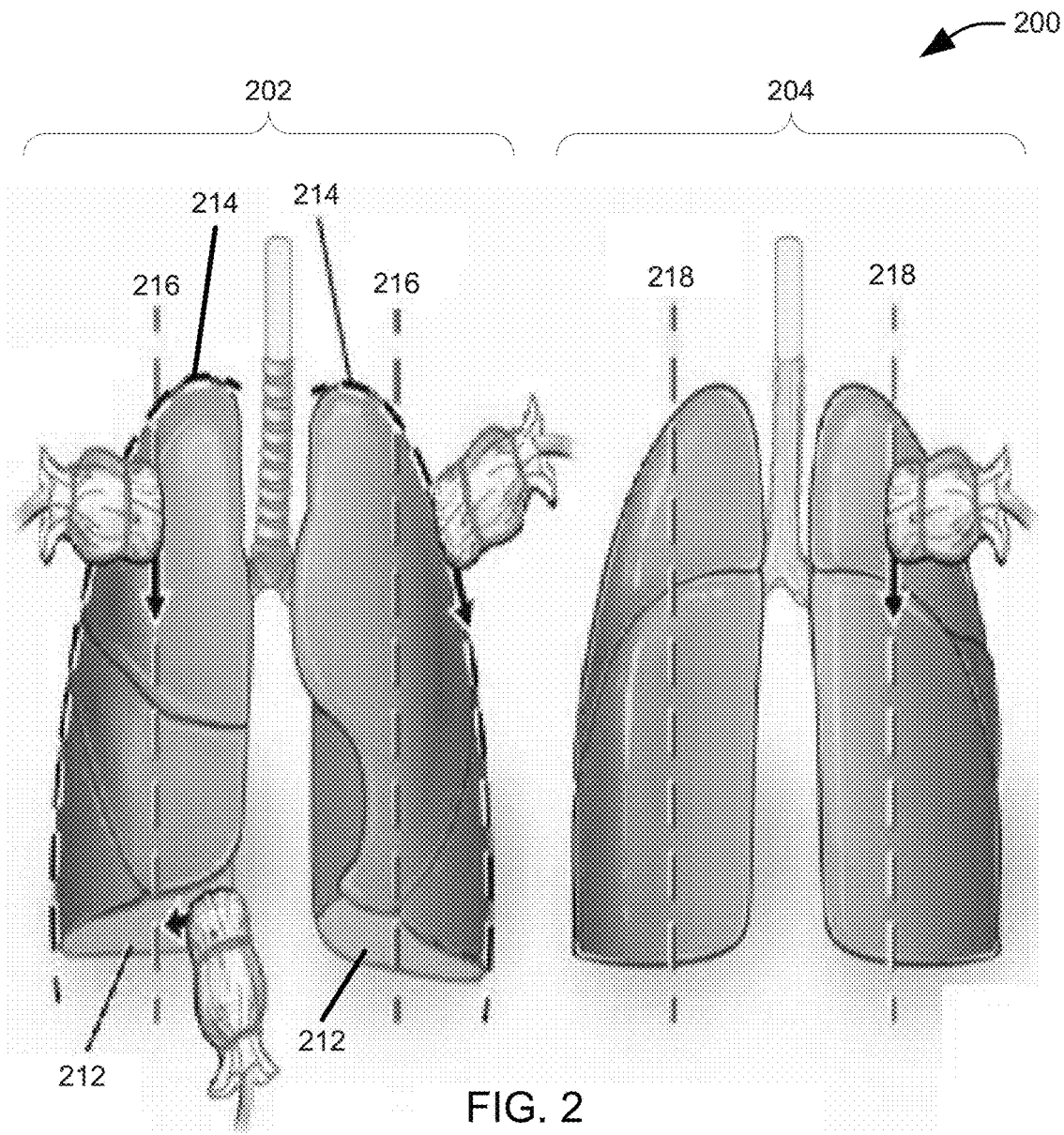
FIG. 2 is an image of a pair of lungs with the regions along which the plurality of images are taken.

FIG. 1 illustrates a system 100 for evaluating a lung via ultrasound. The system 100 includes an ultrasound imager 102 that can be manipulated, relative to the lung, to provide a plurality of images of the lung at a plurality of locations on the lung, such that each of the plurality of locations is represented by at least one of the plurality of images. In one example, the ultrasound imager 102 includes a six to thirteen megahertz probe for capturing ultrasound images. In one implementation, the plurality of locations are selected along four lines passing through the anterior, lateral, posterior, and diaphragmatic surfaces of each lung. FIG. 2 is an image of a pair of lungs 200 with the regions along which the plurality of images are taken. The image shows an anterior view 202 of the lungs and a posterior view 204 of the lungs. Images can be taken in a line along the diaphragmatic surface 212 of each lung, the lateral line 214 of each lung, the anterior line 216 of each lung, and the posterior line 218 of each lung. It will be appreciated that the plurality of locations will not necessarily include locations along all four lines, but that locations along all four lines can be used to provide local information around various lobes of the lung. Accordingly, the plurality of images taken at the ultrasound imager 102 collectively represent the overall condition of the lung, but can also be used to determine localized issues with the lung.

The system 100 further includes a processor 104 and a non-transitory computer readable medium 110 storing executable instructions for evaluating the condition of the lung based on the images from the ultrasound imager 102. The executable instructions include a grader interface 112 that receives, for each of the plurality of locations, data representing the image or images taken at that location and provides a grade representing the amount of B-line distortion in each image. In one implementation, the grader interface 112 can comprise an input interface for receiving data representing grades assigned by a human expert. Alternatively, the grader interface 112 can comprises an interface for receiving the ultrasound image and an appropriate expert system to generate the grade from the image. In one implementation, six grades are utilized, a first grade indicating minimal B-line artifact, a second grade indicating moderate B-line artifact, a third grade indicating significant B-line artifact, a fourth grade indicating severe B-line artifact, a fifth grade indicating the absence of B-line artifact, and a sixth grade indicating consolidation, that is, a replacement of air with liquid or solid material, at the imaged location.

Figure 3:
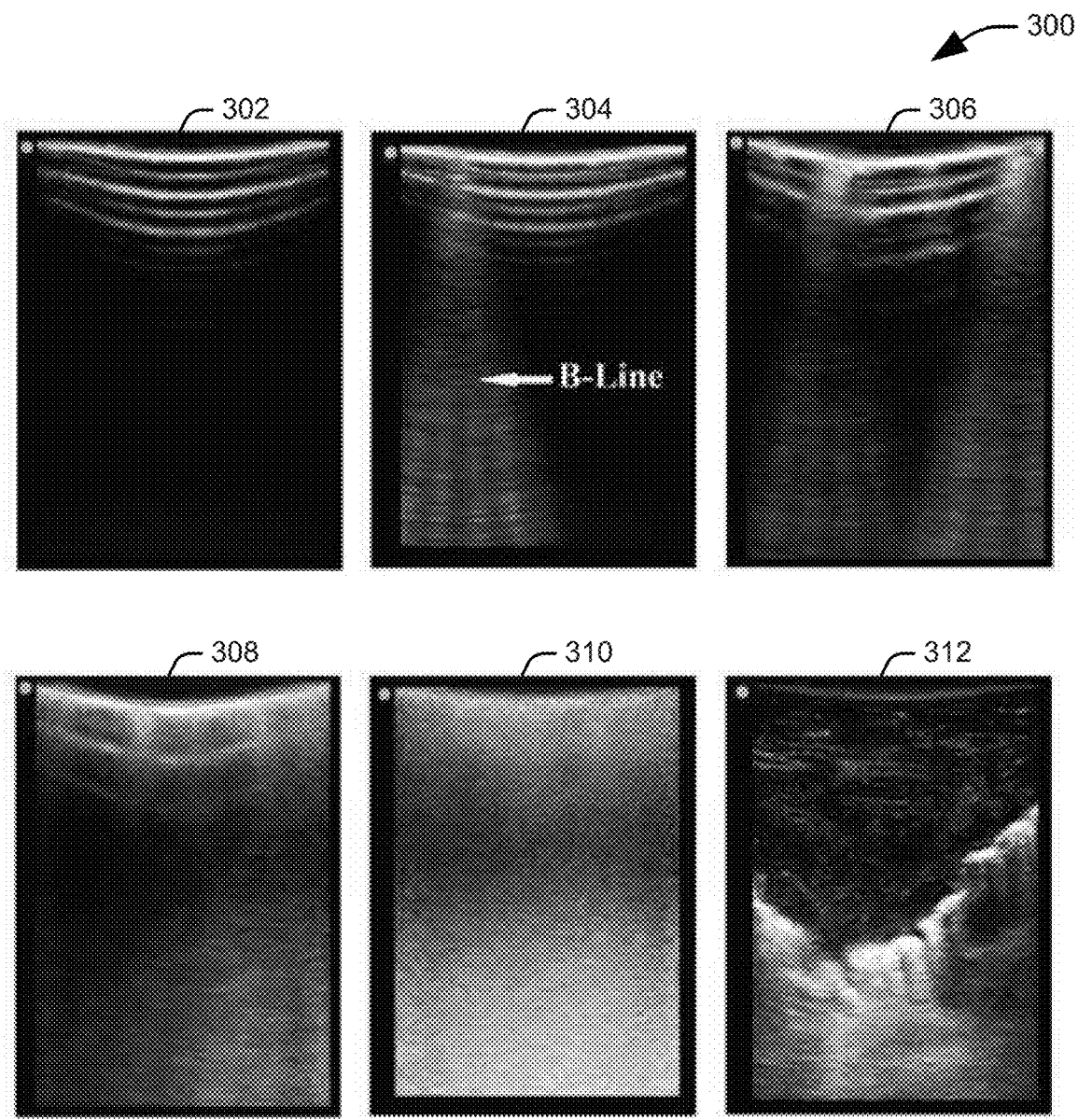
FIG. 3 illustrates a series of example images representing each of the six grades used in one implementation of the system.

FIG. 3 illustrates a series of example images 300 representing each of the six grades used in one implementation of the system 100. A first image 302 shows no visible B-line artifact, and would be given the fifth grade. A second image 304 shows minimal B-line artifact, indicated in the image by a white arrow, within the region of interest at the bottom of the image in which B-line artifact would be expected, and would be given the first grade. In one example, the first grade is given when B-lines are present, but only over twenty-five percent of the region of interest or less. A third image 306 shows moderate B-line artifact and would be given the second grade. In one example, the second grade is given when B-lines are present over an area including between twenty-five and fifty percent of the region of interest. A fourth image 308 shows significant B-line artifact and would be given the third grade. In one example, the third grade is given when B-lines are present over an area including between fifty and seventy-five percent of the region of interest. A fifth image 310 shows severe B-line artifact and would be given the fourth grade. In one example, the fourth grade is given when B-lines are present over an area greater than seventy-five percent of the region of interest. A sixth image 312 illustrates consolidation within the lung.

Returning to FIG. 1, the grades received at the grader interface 112 are provided to a score calculator 114. The score calculator 114 determines a composite score representing the condition of the lung from the plurality of grades. The determined score is then provided to a user at an output device (not shown), such as a display, speaker, or similar device, via a user interface 116. In one implementation, the grade is assigned as a continuous value for each image. In such a case, the composite score can be determined as an average (e.g., mean or median) of the score for each image. In another implementation, the grade can be categorical, and each category can have an associated score that is used to calculate the composite score. In the example using the six grades described above, the composite score can be generated as:

$$\text{Score} = \frac{N_{G_1} + 2*N_{G_2} + 3*N_{G_3} + 4*N_{G_4} + 5*N_C}{N_{tot}} \quad \text{Eq. 1}$$

where $N_{G_1}$ is the number of images with the first grade, $N_{G_2}$ is the number of images with the second grade, $N_{G_3}$ is the number of images with the third grade, $N_{G_4}$ is the number of images with the fourth grade, $N_C$ is the number of images with consolidation, and $N_{tot}$ is the total number of images.

Figure 4:
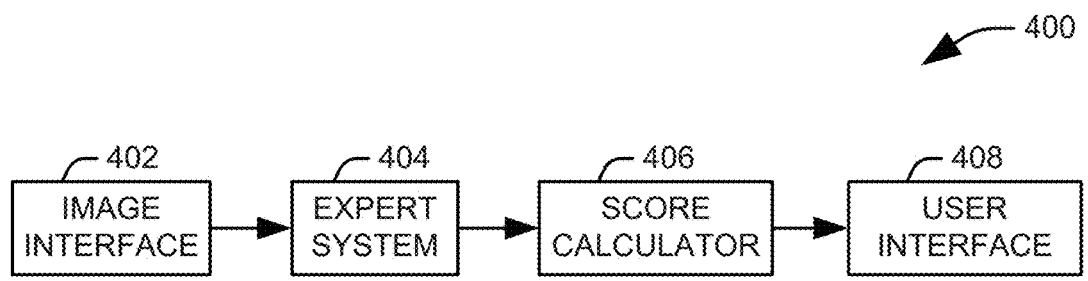
FIG. 4 illustrates one example of image analysis software that might be utilized as part of a system for evaluating lungs in accordance with an aspect of the invention.

FIG. 4 illustrates one example of image analysis software 400 that might be utilized as part of a system for evaluating lungs in accordance with an aspect of the invention. Specifically, the illustrated software 400 can represent the executable instructions stored on the non-transitory computer readable medium 110 of FIG. 1. The illustrated implementation 400 includes an image interface 402 that receives images from an ultrasound imager (not shown). The image interface 402 can include appropriate algorithms for formatting and otherwise preparing the image for analysis at an associated expert system 404.

In one implementation, the expert system 404 can comprise one or more pattern recognition classifiers, each of which utilize a set of extracted features from the image to determine an appropriate grade for the image. The extracted features can include, for example, percentages of white pixels in various regions of the image, a length of edges located within various regions of the image, and any other suitable features for measuring the degree of B-line artifact within each image. Where multiple classifiers are used, an arbitration element can be utilized to provide a coherent result from the plurality of classifiers. Each classifier is trained on a plurality of training images representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, boosting and bagging methods, rule based systems, or artificial neural networks.

For example, a SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. In one implementation, the SVM can be implemented via a kernel method using a linear or non-linear kernel.

An artificial neural network (ANN) classifier comprises a plurality of nodes having a plurality of interconnections. The values from the extracted features are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A convolutional neural network (CNN) is a type an ANN classifier that is generally not fully connected between layers, for example, a given input node may be connected to only a proper subset of the nodes in a hidden layer. This partial connection allows the CNN to learn various convolutional kernels that operate much like the kernels used in image filtering. These learned kernels effectively operate as the features for discriminating among classes, and as a result, the input into the CNN is generally the raw chromatic values for the pixels comprising the image.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used. In another implementation, the expert system 404 can include a regression model configured to provide calculate a parameter representing the score for the image from extracted features.

A score calculator 406 determines a composite score representing the condition of the lung from the plurality of grades. The determined score is then provided to a user at an output device (not shown), such as a display, speaker, or similar device, via a user interface 408. In one implementation, for example, when the expert system 404 is implemented as a regression model, the grade is assigned as a continuous value for each image. In such a case, the composite score can be determined as an average (e.g., mean or median) of the score for each image. In another implementation, for example, when the expert system 404 is implemented as a classifier, the grade can be categorical, and each category can have an associated score that is used to calculate the composite score as an average of the assigned scores. In a third implementation, each of the grades and the composite scores can be categorical, with the composite score selected as a mode of the assigned grades.

Figure 5:
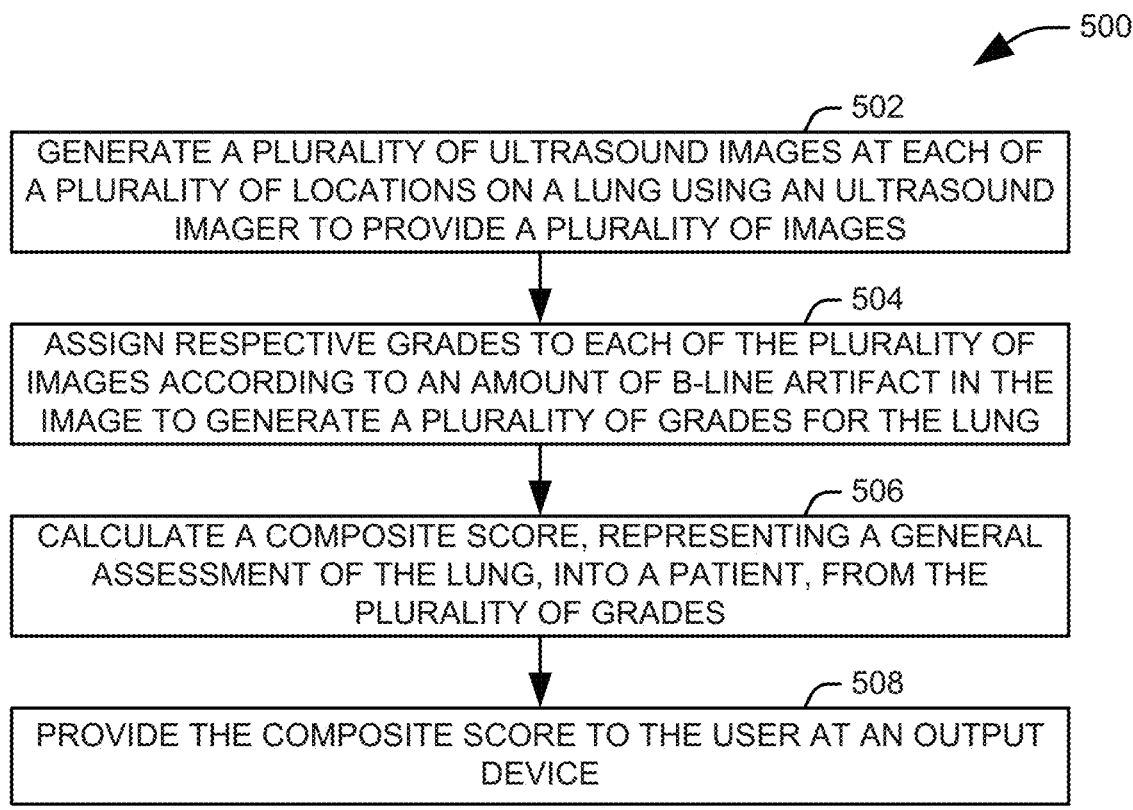
FIG. 5 illustrates a method for evaluating a lung via ultrasound.

In view of the foregoing features described above, an example method will be better appreciated with reference to FIG. 5. While, for purposes of simplicity of explanation, the method is shown and described as executing serially, it is to be understood and appreciated that the method is not limited by the illustrated order, as parts of the method could occur in different orders and/or concurrently from that shown and described herein.

FIG. 5 illustrates a method 500 for evaluating a lung via ultrasound. At 502, a plurality of ultrasound images are generated at each of a plurality of locations on a lung using an ultrasound imager to provide a plurality of images. In one implementation, each of the plurality of locations lies along one of a line along an anterior surface of the lung, a line along a lateral surface of the lung, a line along a posterior surface of the lung, and a line along a diaphragmatic surface of the lung.

At 504, respective grades are assigned to each of the plurality of images according to an amount of B-line artifact in the image to generate a plurality of grades for the lung. In one implementation, the grades are determined by providing the images to human experts for evaluation. In another implementation, an expert system can be employed to assign a grade for each image according to a set of features extracted from the image. In one example, the possible grades include a first grade indicating minimal B-line artifact, a second grade indicating moderate B-line artifact, a third grade indicating significant B-line artifact, a fourth grade indicating severe B-line artifact, a fifth grade indicating the absence of B-line artifact, and a sixth grade indicating consolidation at the imaged location.

At 506, a composite score for the lung, representing a suitability of the lung for transplant into a patient is calculated from the plurality of grades. In one implementation, a score is assigned to each of the plurality of images according to the grade assigned to the image the scores are averaged across the plurality of images. The average can be any appropriate measure of central tendency, including the arithmetic mean or the median of the scores. In one example, the composite score can instead be categorical, and the mode of the various categorical grades can be selected as the composite score. In one example, a lobe score for each of a plurality of lobes of the lung, representing an amount of extravascular lung water within the lobe, can be determined from a proper subset of the plurality of grades representing locations on or near the lobe. The composite score, as well as any calculated lobe scores, are then provided to a user at an associated output device at 508.

Figure 6:
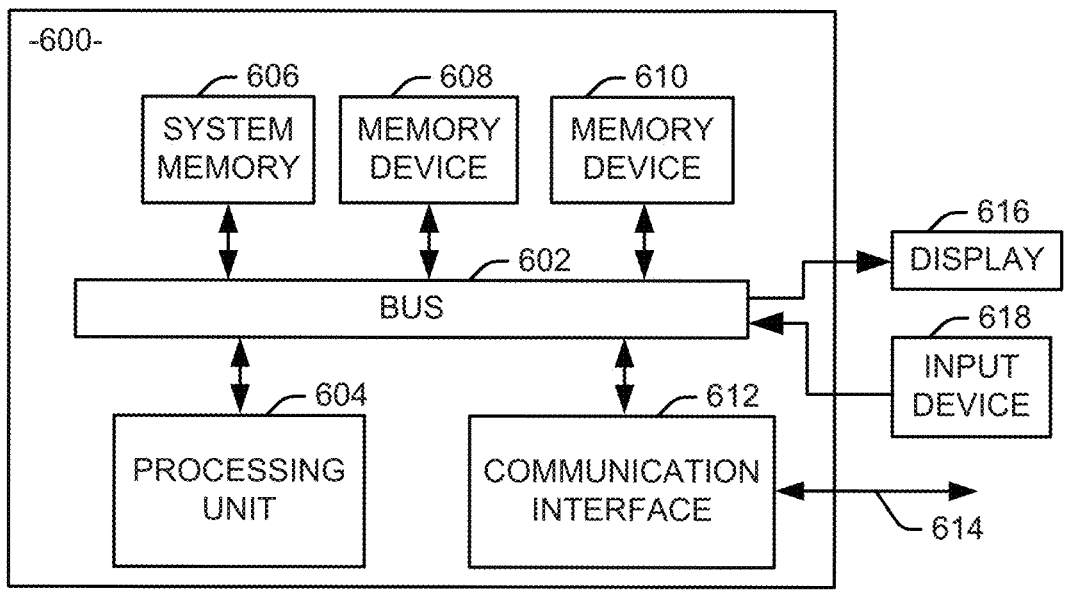
FIG. 6 is a schematic block diagram illustrating an exemplary system of hardware components capable of implementing examples of the systems and methods disclosed in FIGS. 1-5.

FIG. 6 is a schematic block diagram illustrating an exemplary system 600 of hardware components capable of implementing examples of the systems and methods disclosed in FIGS. 1-5. The system 600 can include various systems and subsystems. The system 600 can be a personal computer, a laptop computer, a workstation, a computer system, an appliance, an application-specific integrated circuit (ASIC), a server, a server blade center, a server farm, etc.

The system 600 can includes a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard and/or a mouse). The system bus 602 can be in communication with the processing unit 604 and the system memory 606. The additional memory devices 608 and 610, such as a hard disk drive, server, stand alone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core.

The additional memory devices 606, 608 and 610 can store data, programs, instructions, database queries in text or compiled form, and any other information that can be needed to operate a computer. The memories 606, 608 and 610 can be implemented as computer-readable media (integrated or removable) such as a memory card, disk drive, compact disk (CD), or server accessible over a network. In certain examples, the memories 606, 608 and 610 can comprise text, images, video, and/or audio, portions of which can be available in formats comprehensible to human beings.

Additionally or alternatively, the system 600 can access an external data source or query source through the communication interface 612, which can communicate with the system bus 602 and the communication link 614.

In operation, the system 600 can be used to implement one or more parts of a system for evaluating lungs in accordance with the present invention. Computer executable logic for implementing the lung evaluation system resides on one or more of the system memory 606, and the memory devices 608, 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution, and can, in practice, refer to multiple, operatively connected apparatuses for storing machine executable instructions.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   an ultrasound imager manipulable to image a lung at a plurality of locations to produce a plurality of images;
   a processor; and
   a non-transitory computer readable medium storing executable instructions, the executable instructions comprising:
      a grader interface configured to receive, for each of the plurality of locations, data representing the image or images taken at that location and provide a plurality of grades, each representing the amount of B-line artifact in a corresponding image, wherein the plurality of locations includes at least one location along each of a line along the anterior surface of the lung, a line along the lateral surface of the lung, a line along the posterior surface of the lung, and a line along the diaphragmatic surface of the lung;
      a score calculator configured to determine a composite score representing a general assessment of the lung from the plurality of grades; and
      a user interface configured to provide the composite score to a user at an associated output device.

2. The system of claim 1, wherein the grader interface comprises an input interface for receiving data representing grades assigned by a human expert.

3. The system of claim 1, wherein each of the plurality of grades are selected from a set of six grades comprising a first grade indicating minimal B-line artifact, a second grade indicating moderate B-line artifact, a third grade indicating significant B-line artifact, a fourth grade indicating severe B-line artifact, a fifth grade indicating the absence of B-line artifact, and a sixth grade indicating consolidation at the imaged location.

4. The system of claim 3, wherein the first grade is selected when the B-line artifact is present but covers less than twenty-five percent of a region of interest within the image, the second grade is selected when the B-line artifact covers between twenty-five and fifty percent of the region of interest, the third grade is selected when the B-line artifact covers between fifty and seventy-five percent of the region of interest, and the fourth grade is selected when the B-line artifact covers more than seventy-five percent of the image.

5. The system of claim 3, wherein the score calculator calculates the composite score as:

$$\text{Score} = \frac{N_{G_1} + 2*N_{G_2} + 3*N_{G_3} + 4*N_{G_4} + 5*N_C}{N_{tot}}$$

where $N_{G_1}$ is the number of times that the first grade is selected, $N_{G_2}$ is the number of times that the second grade is selected, $N_{G_3}$ is the number of times that the third grade is selected, $N_{G_4}$ is the number of times that the fourth grade is selected, $N_C$ is the number of images indicating consolidation, and $N_{tot}$ is the total number of images.

6. The system of claim 1, wherein the grader interface comprises an image interface configured to receive the plurality of images and an expert system that utilizes a set of extracted features from the image to determine an appropriate grade for the image.

7. The system of claim 6, the expert system comprising a pattern recognition classifier configured to assign a categorical grade to the image from the set of extracted features.

8. The system of claim 6, the expert system comprising a regression model configured to assign a numerical grade to the image from the set of extracted features.

9. The system of claim 1, wherein the score calculator is configured to determine a location score for each location from the plurality of grades and calculate the composite score as an average of the locations scores for the plurality of locations.

10. A method comprising:
   generating a plurality of ultrasound images at each of a plurality of locations on a lung using an ultrasound imager to provide a plurality of images, the plurality of locations including one of a location along the line along the posterior surface of the lung and a location along the line along the diaphragmatic surface of the lung;
   assigning respective grades to each of the plurality of images according to an amount of B-line artifact in the image to generate a plurality of grades for the lung;
   calculating a composite score for the lung from the plurality of grades, the composite score representing a general assessment of the lung for transplant into a patient; and providing the composite score to a user at an associated output device.

11. The method of claim 10, further comprising calculating a lobe score for each of a plurality of lobes of the lung, representing an amount of extravascular lung water within the lobe, from respective proper subsets of the plurality of grades.

12. The method of claim 10, wherein assigning respective grades to each of plurality of ultrasound images comprises providing the images to human experts for evaluation.

13. The method of claim 10, wherein assigning respective grades to each of plurality of ultrasound images comprises selecting each of the plurality of grades from a set of six grades comprising a first grade indicating minimal B-line artifact, a second grade indicating moderate B-line artifact, a third grade indicating significant B-line artifact, a fourth grade indicating severe B-line artifact, a fifth grade indicating the absence of B-line artifact, and a sixth grade indicating consolidation at the imaged location.

14. The method of claim 13, wherein calculating a composite score for the lung from the plurality of grades comprises assigning a score to each of the plurality of images according to the grade assigned to the image and averaging the scores across the plurality of images.

15. The method of claim 10, wherein assigning respective grades to each of plurality of ultrasound images comprises providing the images to an expert system.

16. The method of claim 10, wherein each of the plurality of locations lies along one of a line along an anterior surface of the lung, a line along a lateral surface of the lung, the line along a posterior surface of the lung, and the line along a diaphragmatic surface of the lung.

17. A computer program product, storing instructions executable by an associated processor to evaluate a plurality of ultrasound images of a lung, the executable instructions comprising:
a grader interface configured to receive, for each of the ultrasound images, data representing the image, and select a grade representing the amount of B-line artifact in the images from a set of six grades comprising a first grade indicating minimal B-line artifact, a second grade indicating moderate B-line artifact, a third grade indicating significant B-line artifact, a fourth grade indicating severe B-line artifact, a fifth grade indicating the absence of B-line artifact, and a sixth grade indicating consolidation at the imaged location;
a score calculator configured to determine a composite score representing a general assessment of the lung from the plurality of grades; and
a user interface configured to provide the composite score to a user at an associated output device.

18. The computer program product of claim 17, wherein the grader interface comprises an image interface configured to receive the plurality of images and an expert system that utilizes a set of extracted features from the image to determine the grade for the image.

19. The computer program product of claim 17, wherein the first grade is selected when the B-line artifact is present but covers less than twenty-five percent of a region of interest within the image, the second grade is selected when the B-line artifact covers between twenty-five and fifty percent of the region of interest, the third grade is selected when the B-line artifact covers between fifty and seventy-five percent of the region of interest, and the fourth grade is selected when the B-line artifact covers more than seventy-five percent of the image.

20. The computer program product of claim 17, wherein the score calculator calculates the composite score as:

$$\text{Score} = \frac{N_{G_1} + 2*N_{G_2} + 3*N_{G_3} + 4*N_{G_4} + 5*N_C}{N_{tot}}$$

where $N_{G_1}$ is the number of times that the first grade is selected, $N_{G_2}$ is the number of times that the second grade is selected, $N_{G_3}$ is the number of times that the third grade is selected, $N_{G_4}$ is the number of times that the fourth grade is selected, $N_C$ is the number of images indicating consolidation, and $N_{tot}$ is the total number of images.

* * * * *